US010258426B2

(12) United States Patent
Silva et al.

(10) Patent No.: US 10,258,426 B2
(45) Date of Patent: Apr. 16, 2019

(54) SYSTEM AND METHOD FOR VIRTUAL REALITY DATA INTEGRATION AND VISUALIZATION FOR 3D IMAGING AND INSTRUMENT POSITION DATA (71) Applicant: Washington University, St. Louis, MO (US)

(72) Inventors: Jonathan Silva, St. Louis, MO (US); Jennifer Silva, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/918,418

(22) Filed: Mar. 12, 2018

(65) Prior Publication Data
US 2018/0200018 A1 Jul. 19, 2018

Related U.S. Application Data (63) Continuation of application No. PCT/US2017/023221, filed on Mar. 20, 2017.
(Continued)

(51) Int. Cl.
*A61B 90/00* (2016.01)
*G06T 15/20* (2011.01)
(Continued)

(52) U.S. Cl.
CPC ............. *A61B 90/37* (2016.02); *A61B 5/042* (2013.01); *A61B 5/066* (2013.01); *A61B 5/743* (2013.01);
(Continued)

(58) Field of Classification Search
CPC ...... A61B 2034/2055; A61B 2034/105; A61B 2034/107; A61B 2034/252; A61B 34/10; A61B 34/20
See application file for complete search history.

(56) References Cited

U.S. PATENT DOCUMENTS 5,662,108 A 9/1997 Budd
6,323,971 B1 11/2001 Klug
(Continued)

FOREIGN PATENT DOCUMENTS

WO 2015149042 A1 10/2015
WO 2016133644 A1 8/2016
(Continued)

OTHER PUBLICATIONS

PCT International Search Report and Written Opinion, Application No. PCT/US2017/023221, dated Aug. 3, 2017, 9 pps.

*Primary Examiner* — Baisakhi Roy
(74) *Attorney, Agent, or Firm* — Armstrong Teasdale LLP (57) ABSTRACT Systems and methods for virtual reality or augmented reality (VR/AR) visualization of 3D medical images using a VR/AR visualization system are disclosed. The VR/AR visualization system includes a computing device operatively coupled to a VR/AR device, and the VR/AR device includes a holographic display and at least one sensor. The holographic display is configured to display a holographic image to an operator. The computing device is configured to receive at least one stored 3D image of a subject's anatomy and at least one real-time 3D position of at least one surgical instrument. The computing device is further configured to register the at least one real-time 3D position of the at least one surgical instrument to correspond to the at least one 3D image of the subject's anatomy, and to generate the holographic image comprising the at least one real-time position of the at least one surgical instrument overlaid on the at least one 3D image of the subject's anatomy.

30 Claims, 8 Drawing Sheets

Related U.S. Application Data (60) Provisional application No. 62/310,969, filed on Mar. 21, 2016.

(51) Int. Cl.

| | | |
|---|---|---|
| *G06T 17/20* | (2006.01) | |
| *G06F 3/01* | (2006.01) | |
| *G06T 19/00* | (2011.01) | |
| *A61B 5/042* | (2006.01) | |
| *A61B 34/20* | (2016.01) | |
| *A61B 5/00* | (2006.01) | |
| *A61B 5/06* | (2006.01) | |
| *G06F 19/00* | (2018.01) | |
| *A61B 18/02* | (2006.01) | |
| *A61B 18/14* | (2006.01) | |
| *A61B 18/00* | (2006.01) | |

(52) U.S. Cl.
CPC .............. *A61B 5/745* (2013.01); *A61B 34/20* (2016.02); *A61B 90/361* (2016.02); *G06F 3/017* (2013.01); *G06F 19/00* (2013.01); *G06T 15/205* (2013.01); *G06T 17/20* (2013.01); *G06T 19/00* (2013.01); *G06T 19/006* (2013.01); *A61B 18/02* (2013.01); *A61B 18/1492* (2013.01); *A61B 2018/00351* (2013.01); *A61B 2018/00577* (2013.01); *A61B 2018/00642* (2013.01); *A61B 2018/00839* (2013.01); *A61B 2018/0212* (2013.01); *A61B 2034/2051* (2016.02); *A61B 2034/2063* (2016.02); *A61B 2034/2065* (2016.02); *A61B 2090/365* (2016.02); *A61B 2090/367* (2016.02); *A61B 2090/368* (2016.02); *A61B 2090/376* (2016.02); *A61B 2090/3782* (2016.02); *G06T 2210/41* (2013.01); *G06T 2219/004* (2013.01); *G06T 2219/024* (2013.01)

(56) References Cited

U.S. PATENT DOCUMENTS

| | | | |
|---|---|---|---|
| 6,631,016 B1 | 10/2003 | Klug | |
| 7,189,208 B1 | 3/2007 | Beatty | |
| 7,376,903 B2 | 5/2008 | Morita | |
| 7,725,157 B2 | 5/2010 | Dumoulin | |
| 7,729,752 B2 | 6/2010 | Harlev | |
| 7,774,044 B2 | 8/2010 | Sauer | |
| 7,957,791 B2 | 6/2011 | Harlev | |
| 7,957,792 B2 | 6/2011 | Harlev | |
| 7,966,058 B2 | 6/2011 | Xue | |
| 7,983,733 B2 | 7/2011 | Viswanathan | |
| 8,038,625 B2 | 10/2011 | Afonso | |
| 8,050,739 B2 | 11/2011 | Eck | |
| 8,103,338 B2 | 1/2012 | Harlev | |
| 8,214,018 B2 | 7/2012 | Markowitz | |
| 8,224,432 B2 | 7/2012 | MacAdam | |
| 8,401,625 B2 | 3/2013 | Harlev | |
| 8,494,608 B2 | 7/2013 | Markowitz | |
| 8,500,284 B2 | 8/2013 | Rotschild | |
| 8,504,136 B1 | 8/2013 | Sun | |
| 8,571,647 B2 | 10/2013 | Harlev | |
| 8,615,287 B2 | 12/2013 | Harlev | |
| 8,849,384 B2 | 9/2014 | Greenspan | |
| 8,849,389 B2 | 9/2014 | Ramanathan | |
| 8,860,753 B2 | 10/2014 | Bhandarkar | |
| 8,934,962 B2 | 1/2015 | Saadat | |
| 8,989,842 B2 | 3/2015 | Li | |
| 8,996,173 B2 | 3/2015 | Itkowitz | |
| 9,122,053 B2 | 9/2015 | Geisner | |
| 9,123,155 B2 | 9/2015 | Cunningham | |
| 9,265,442 B2 | 2/2016 | Wedan | |
| 9,360,934 B2 | 6/2016 | Ruiz Morales | |
| 9,406,171 B2 | 8/2016 | Broaddus | |
| 9,412,205 B2 | 8/2016 | Mullins | |
| 9,417,452 B2 | 8/2016 | Schowengerdt | |
| 9,439,736 B2 | 9/2016 | Olson | |
| 9,445,742 B2 | 9/2016 | Slizynski | |
| 9,498,146 B2 | 11/2016 | Harlev | |
| 9,510,769 B2 | 12/2016 | Harlev | |
| 9,538,962 B1 | 1/2017 | Hannaford | |
| 9,541,901 B2 | 1/2017 | Rotschild | |
| 9,560,318 B2 | 1/2017 | Reina | |
| 9,594,347 B2 | 3/2017 | Kaufman | |
| 9,662,033 B2 | 5/2017 | Severino | |
| 9,720,235 B2 | 8/2017 | Border | |
| 2004/0024311 A1* | 2/2004 | Quaid, III | A61B 17/3403 600/428 |
| 2004/0106916 A1* | 6/2004 | Quaid | A61B 34/71 606/1 |
| 2005/0080336 A1* | 4/2005 | Byrd | A61B 8/065 600/428 |
| 2005/0283079 A1* | 12/2005 | Steen | A61B 8/14 600/447 |
| 2007/0248319 A1* | 10/2007 | Sakaguchi | A61B 6/461 386/219 |
| 2007/0270680 A1* | 11/2007 | Sheffer | A61B 90/36 600/407 |
| 2011/0069159 A1 | 3/2011 | Soler | |
| 2011/0082351 A1* | 4/2011 | Razzaque | A61B 5/015 600/301 |
| 2011/0107270 A1 | 5/2011 | Wang | |
| 2012/0327186 A1 | 12/2012 | Kitamura | |
| 2013/0038707 A1 | 2/2013 | Cunningham | |
| 2013/0154913 A1 | 6/2013 | Genc | |
| 2013/0172906 A1 | 7/2013 | Olson | |
| 2013/0267838 A1 | 10/2013 | Fronk | |
| 2014/0222526 A1 | 8/2014 | Shakil | |
| 2014/0275760 A1 | 9/2014 | Lee | |
| 2014/0282008 A1 | 9/2014 | Verard | |
| 2015/0173846 A1 | 6/2015 | Schneider | |
| 2015/0248793 A1 | 9/2015 | Abovitz | |
| 2015/0302665 A1 | 10/2015 | Miller | |
| 2015/0324114 A1 | 11/2015 | Hurley | |
| 2015/0366628 A1 | 12/2015 | Ingmanson | |
| 2016/0077489 A1 | 3/2016 | Kaufman | |
| 2016/0147308 A1 | 5/2016 | Gelman | |
| 2016/0203359 A1 | 7/2016 | von und zu Liechtenstein | |
| 2016/0249989 A1 | 9/2016 | Devam | |
| 2016/0278868 A1* | 9/2016 | Berend | A61B 34/10 |
| 2017/0027651 A1 | 2/2017 | Esterberg | |
| 2017/0090420 A1 | 3/2017 | Rotschild | |
| 2017/0161893 A1 | 6/2017 | Carnes | |
| 2017/0172696 A1 | 6/2017 | Saget | |

FOREIGN PATENT DOCUMENTS

| | | |
|---|---|---|
| WO | 2016151506 A1 | 9/2016 |
| WO | 2016207628 A1 | 12/2016 |
| WO | 2017145155 A1 | 8/2017 |
| WO | 2017145156 A2 | 8/2017 |
| WO | 2017145158 A1 | 8/2017 |
| WO | 2017145156 A3 | 11/2017 |

* cited by examiner

SYSTEM AND METHOD FOR VIRTUAL REALITY DATA INTEGRATION AND VISUALIZATION FOR 3D IMAGING AND INSTRUMENT POSITION DATA

CROSS-REFERENCE TO RELATED APPLICATION

This application is a continuation of PCT Application No. PCT/US2017/023221, filed Mar. 20, 2017, which claims the benefit of U.S. Provisional Application No. 62/310,969, filed Mar. 21, 2016, both of which are hereby incorporated by reference herein in their entirety.

BACKGROUND

A central issue for interventional surgical procedures remains visualization of the unexposed anatomy and localization of medical devices within the organs and vessels, such as catheters, stents, probes, and the like. As procedures move away from maximal exposure towards being minimally invasive, the requirements for enhanced visualization are more profound. An example is minimally invasive transcatheter ablation for cardiac arrhythmias.

In healthy hearts, organized electrical excitation causes heart contraction. When this electrical activity becomes irregular, the heart can no longer pump efficiently and patients experience dizziness, fainting, and/or sudden death. Statistics from the Centers for Disease Control and Prevention have estimated that in the United States sudden cardiac death claims more than 600,000 victims every year. Erratic, irregular electrical cardiac activity is called an arrhythmia, and is often caused by abnormal electrical connections in the heart. Cardiac arrhythmias affect people of all ages.

These short circuits can be effectively removed by applying one or more energy pulses to a selected region of the heart through a catheter that is placed in the heart, known as a transcatheter ablation. Non-limiting examples of types of energy pulses that may be applied using a transcatheter ablation include radiofrequency energy pulses, cryoenergy pulses, and high frequency ultrasound pulses. A mainstay of modern arrhythmia therapy, ablation procedures require multiple catheters to be inserted into the heart to record electrical activity, identify key locations responsible for the arrhythmia, and ablate tissue using either radiofrequency energy or cryotherapy. Currently, ablation procedures are complicated by the masking of the heart by the chest wall and separation of data (i.e., electrical signals, anatomic location, etc.) in the electrophysiology laboratory, requiring the physician to mentally reconstruct a heart model.

These procedures have been enhanced significantly by the development of electroanatomic mapping systems that construct a point-by-point map of the interior surface of the heart (endocardium) incorporating both anatomic location and the local electrical signal. However, these systems are limited by the display of key measurements on multiple two-dimensional screens. The skill to mentally relate electrical recordings to the overall multi-dimensional cardiac anatomy remains a key challenge in the training of cardiac electrophysiologists and intra-procedural collaboration. It is therefore intensely difficult to train new physicians, and significant skill-dependent variability in outcomes is common.

SUMMARY

In one aspect, a VR/AR visualization system is provided. The VR/AR visualization system includes a VR/AR device that includes a holographic display configured to display a holographic image to an operator, and a computing device operatively coupled to the VR/AR device. The computing device includes a non-volatile memory and a processor. The computing device is configured to receive at least one stored 3D image of a subject's anatomy, to receive at least one real-time 3D position of at least one surgical instrument, to register the at least one real-time 3D position of the at least one surgical instrument to correspond to the at least one stored 3D image of the subject's anatomy; and to generate the holographic image. The holographic image includes the at least one real-time 3D position of the at least one surgical instrument overlaid on the at least one 3D image of the subject's anatomy.

In another aspect, a method of VR/AR visualization of 3D medical images is provided. The method includes receiving, using a computing device, at least one stored 3D image of a subject's anatomy. The computing device is operatively coupled to a VR/AR device, and the VR/AR device includes a holographic display and at least one sensor. The method further includes receiving, using the computing device, at least one real-time 3D position of at least one surgical instrument, registering the at least one real-time 3D position of the at least one surgical instrument to correspond to the at least one stored 3D image of the subject's anatomy; and displaying, using the holographic display, a holographic image comprising the at least one real-time 3D position of the at least one surgical instrument overlaid on the at least one 3D image of the subject's anatomy to an operator.

In an additional aspect, at least one non-transitory computer-readable storage media for providing VR/AR visualization of three-dimensional medical images to an operator is provided. The computer-readable storage media has computer-executable instructions embodied thereon, wherein, when executed by at least one processor, the computer-executable instructions cause the processor to receive at least one stored 3D image of a subject's anatomy, receive at least one real-time 3D position of at least one surgical instrument, register the at least one real-time 3D position of the at least one surgical instrument to correspond to the at least one stored 3D image of the subject's anatomy, and display a holographic image. The holographic image includes the at least one real-time 3D position of the at least one surgical instrument overlaid on the at least one 3D image of the subject's anatomy to an operator.

In an aspect, the disclosure is a virtual reality/augmented reality (VR/AR) system for procedures that occur within portions of a patient's body. In one aspect, the disclosure is a VR/AR system for medical procedures that occur within hard to view, as well as access, portions of the human anatomy. In an aspect, the VR/AR system provides a multi-dimensional experience for a user (e.g., an operator) during the procedures, with a patient-specific 3D representation of the patient's internal human organ/system in addition to other procedure relevant data. In an aspect, the 3D representation and additional information can be presented in an augmented reality environment. In other aspects, such information can be provided in a VR/AR environment. In addition, the system is able to map and represent the real-time positioning of an instrument (e.g. a catheter) used during the procedure. The 3D representation and the relevant data are configured to be presented and allow interaction with the user such that the user does not need to communicate with any other person nor break sterility. For instance, the user can provide commands to the system without physically contacting an input device with any part of the user's body such as the user's hands.

In an exemplary aspect, the VR/AR system is for cardiac interventional procedures. The system provides a patient-specific 3D model of the heart of the patient in real time as the procedure is occurring, including the ability to track positioning of catheters used within the patient's heart. Additional information can be provided to the user through other senses (e.g., auditory signals) in a manner as described below.

In one aspect, the VR/AR system receives, using a computing device, at least one stored 3D image of a subject's anatomy (e.g. a patient's anatomy). The computing device is coupled to a VR/AR device that comprises a holographic display and at least one sensor. The computing device receives at least one real-time 3D position of at least one surgical instrument. The at least one real-time 3D position of at least one surgical instrument is registered to correspond to the at least one stored 3D image of a subject's anatomy. The holographic display displays a holographic image comprising the at least one real-time 3D position of at least one surgical instrument overlaid on the at least one 3D image of a subject's anatomy to an operator.

In another aspect, the VR/AR system generates a first 3D image of an electroanatomic visualization representing a cardiovascular organ of a subject in 3D by processing a first set of sensor data generated by a catheter inserted inside the cardiovascular organ. The first 3D image is provided to a holographic display including, but not limited to, a head-mounted display (HMD) worn by an operator to display the electroanatomic visualization in a field of view of the operator. A second set of sensor data is received from an input device, where the second set of sensor data is indicative of motion of a body part of the operator to interact with the electroanatomic visualization. A path of the motion of the body part is determined by processing the second set of sensor data. An angle of rotation for the electroanatomic visualization is determined based on the path of motion. A second 3D image is provided to the HMD to update the display of the electroanatomic visualization by rotating the cardiovascular organ by the angle of rotation in the field of view of the operator.

These and other objects and advantages of the invention will become apparent from the following detailed description of the preferred embodiment of the invention. Both the foregoing general description and the following detailed description are exemplary and explanatory only and are intended to provide further explanation of the invention as claimed.

The accompanying drawings are included to provide a further understanding of the disclosure and are incorporated in and constitute part of this specification, illustrate several embodiments of the disclosure and together with the description serve to explain the principles of the disclosure.

DETAILED DESCRIPTION OF THE INVENTION

In the following detailed description of the preferred embodiments, reference is made to the accompanying drawings, which form a part hereof: and within which are shown by way of illustration specific embodiments by which the disclosure may be practiced. It is to be understood that other embodiments may be utilized and structural changes may be made without departing from the scope of the disclosure.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, aspects of the current disclosure may take the form of an entirely hardware embodiment, an entirely software embodiment, or an embodiment combining software and hardware aspects. In an aspect, the current disclosure can include a combination of physical components configured to perform certain steps and functions (e.g., obtaining electroanatomical measurements, etc.) that are controlled by a combination of hardware and software components. Furthermore, components of the methods and systems may take the form of a computer program product on a computer-readable non-transitory storage medium having computer-readable program instructions (e.g., computer software) embodied in the storage medium. Any suitable computer-readable storage medium may be utilized including hard disks, CD-ROMs, optical storage devices, flash storage devices, solid state storage devices, and magnetic storage devices.

Further, components and methods utilized by the disclosure as described below can be performed in a program environment, which may incorporate a general purpose computer or a special purpose device, such as a hardware appliance, controller, or handheld computer. In addition, the techniques of the components described herein can be implemented using a variety of technologies known in the art. For example, the methods may be implemented in software executing on a computer system, or implemented in hardware utilizing either a combination of microprocessors or other specially designed application specific integrated circuits, programmable logic devices, or various combinations thereof.

Some aspects of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a non-transitory computer readable memory that can direct a computer or other programmable data processing apparatus to function in a particular manner, such that the instructions stored in the computer-readable memory produce an article of manufacture including computer readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In various aspects, the disclosure is directed to a virtual reality and/or augmented reality (VR/AR) system, discussed in detail below. While the term virtual reality is used throughout to describe the system, a person of skill in the art would understand that in the generic use of the term, virtual reality may include virtual reality (VR) and augmented reality (AR). In some instances, the term "VR/AR" will be used to identify the system. Therefore, when the term "virtual reality" or "VR/AR" is used herein, it should be understood to encompass all types of modified realities, unless specifically distinguished.

"Virtual reality", as used herein, refers to a method of displaying and/or interacting with one or more elements representing computer-generated data. Typically, all elements visible within a field of view of a virtual reality display are computer-generated elements.

"Augmented reality", as used herein, refers to a method of displaying and/or interacting with one or more elements representing computer-generated data. Augmented reality is a blend of virtual reality and real life, wherein a typical augmented reality display includes one or more computer-generated elements overlaid over the real-life objects visible by an operator. The term "augmented reality", as used herein, may further include "mixed reality", a term that refers to the augmented reality display method that specifically includes an ability for a user or operator to interact with the computer-generated elements.

"Holographic display", as used herein, refers to a method of displaying and/or interacting with a virtual 3D object in which the virtual 3D object is dynamically updated to modify an operator's view of the virtual 3D object in response to movements of the operator, or operator requested modifications of the view of the virtual 3D object, such as magnified/reduced, translated/rotated, cross-sectioned views of the virtual 3D object, etc.

The disclosure is directed to a VR/AR visualization system 10 (also referred to herein as a VR/AR system 10 or system 10) for visualization and manipulation of 3D imaging data as well as additional information including, but not limited to, 2D imaging data, vital sign data, and subject demographic data in association with medical diagnostic and treatment procedures that occur within hard to view/access portions of a subject's anatomy. By way of non-limiting example, the VR/AR visualization system 10 can be utilized for procedures within the heart, gastrointestinal system, ear canal, and other types of anatomy or biological systems. While the embodiments described below are directed to a VR/AR visualization system 10 associated with cardiac interventional procedures, one skilled in the art would recognize that using other 3D localization or pose estimation modalities, including, but not limited to, impedance-based localization, magnetic localization, marker-based localization, or 3D ultrasound in combination with the VR/AR visualization system 10 described herein could be readily extended to diagnostic or interventional procedures in other organ systems and/or other anatomical regions.

Figure 1:
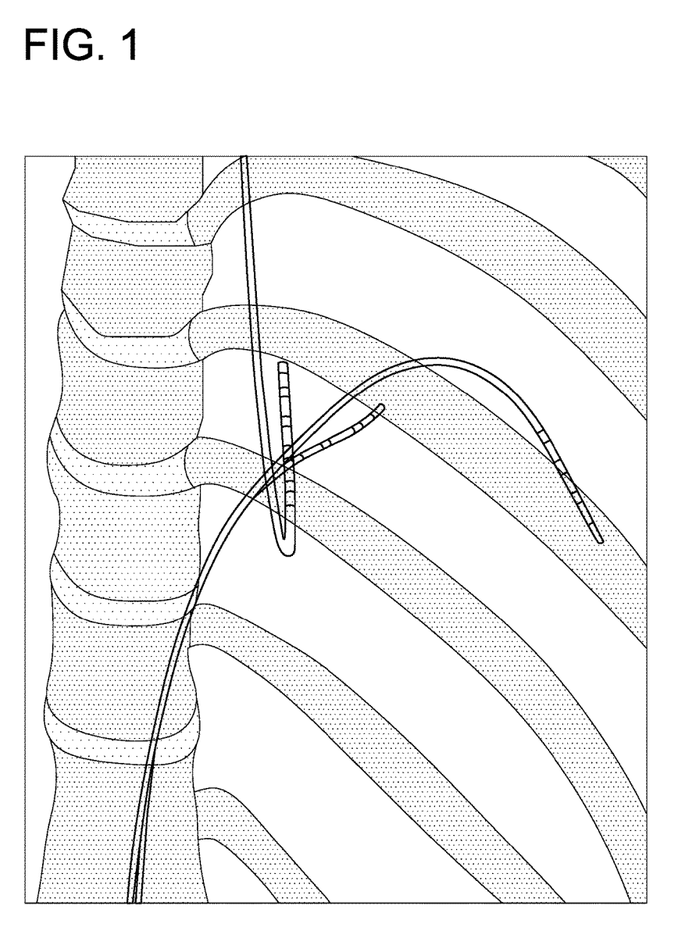
FIG. 1 is a fluoroscopic image used to localize catheters within the heart according to an existing method.
Figure 2:
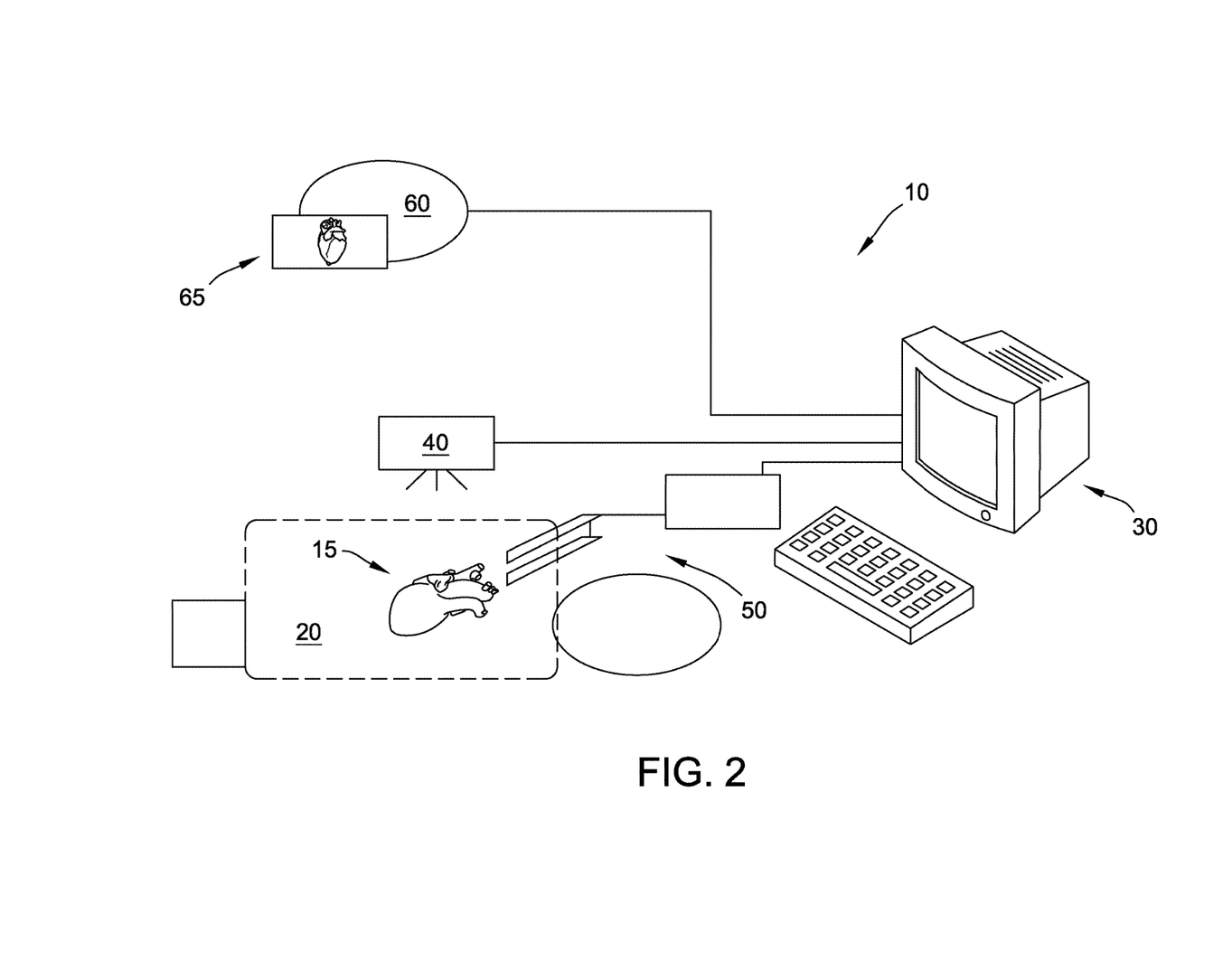
FIG. 2 is a schematic representation of a VR/AR system for internal medical procedures according to one aspect of the disclosure.

In one aspect, the disclosure is directed to a VR/AR visualization system 10 for use in association with cardiac diagnostic procedures and/or cardiac interventional procedures. The VR/AR system 10, via a 3D medical imaging device 40, is able to capture the anatomical features of a heart 15 of a patient 20 (e.g. a subject). In addition, electrical data of the heart 15 can be obtained using one or more electroanatomic mapping devices 50, which are configured to collect electrical data as well as the positioning of associated instruments and the location of the electrical data measurement. Non-limiting examples of instruments associated with the one or more electroanatomic mapping devices 50 include diagnostic catheters, reference catheters, ablation catheters, monitor catheters, noncontact mapping catheters, multielectrode array catheters, multipolar catheters, multipolar circular mapping catheters, and magnetic sensor catheters. In one aspect, data obtained by the one or more electroanatomic mapping devices 50 may be analyzed by an associated electroanatomic mapping system to determine an endocardial map describing the spatial arrangement of the interior surfaces of the atria and ventricles of a heart 15, as well as the spatial arrangement of veins and arteries in relatively close proximity to the heart 15 including, but not limited to a vena cava, an aorta, a pulmonary artery, and the like.

In an aspect, one or more electroanatomic mapping devices 50 may provide for combining at least one 3D map of anatomical features of the heart 15 of the patient 20, obtained using the 3D medical imaging device 40, and at least one 3D endocardial surface map obtained using the one or more electroanatomic mapping devices 50. In one aspect, the 3D coordinate system within which the 3D endocardial surface map is defined may be registered to the coordinate system within which the 3D map of anatomical features of the heart are defined, so that the 3D map of anatomical features and the 3D endocardial surface map are defined within the same 3D coordinate system.

In an aspect, data defining the co-registered 3D map of anatomical features and 3D endocardial surface map produced by the one or more electroanatomic mapping devices 50 may be received by a computing device 30 of the VR/AR visualization system 10. Using the data defining the co-registered 3D map, the computing device 30 generates a 3D model 65 of the heart 15 configured to be displayed within a holographic image produced by the holographic display of a VR/AR device 60.

In one aspect, the holographic image may consist solely of at least a portion of the 3D model 65 of the heart 15. In various other aspects, the computing device 30 of the VR/AR visualization system 10 may receive additional data that may be incorporated into the holographic image for display to the operator on the holographic display of the VR/AR device 60.

In various aspects, the VR/AR system 10 may include multiple VR/AR devices 60. By way of non-limiting example, a first operator may wear a first VR/AR device 60 including, but not limited to, a first head-mounted display, and a second operator may wear a second VR/AR device 60 including, but not limited to, a second head-mounted display. In this non-limiting example, the first and second operators may perform a surgical procedure together on a patient. The first and second VR/AR devices 60 may display different views of the same organ or portion of anatomy of the patient 20. For instance, displayed views of the patient's heart 15 may positioned at different angles based on the location of the corresponding VR/AR device 60 relative to the patient 20.

In various other aspects, additional data may be received by the computing device 30 of the VR/AR visualization system 10 and incorporated into the holographic image. Non-limiting examples of additional data suitable for incorporation into the holographic image include: real-time 3D data defining positions and/or measured values within the coordinate system defining the 3D model 65; real-time 2D data produced by 2D imaging devices such as fluoroscope imaging devices; real-time numerical measurements such as one or more vital signs, pre-determined data such as patient demographic data, and any combination thereof. In these various other aspects, the additional data may be incorporated and/or overlaid on the 3D model 65 of the heart 15, or the additional data may be displayed as a separate element within the holographic image as described in additional detail below.

In one aspect, additional data obtained by the electroanatomic mapping device 50 may be received by the computing device 30 and incorporated into the holographic image. In one aspect, the electroanatomic mapping device may further include an instrument position sensor configured to obtain at least one real-time 3D position of at least one surgical instrument, including, but not limited to, an electrophysiology (EP) catheter. In this aspect, computing device 30 may receive the at least one real-time 3D position of the at least one surgical instrument and generate the holographic image that includes the at least one real-time position of the at least one surgical instrument overlaid on the at least one 3D image of the subject's anatomy, including, but not limited to, the 3D model 65 of the heart 15. In another aspect, the at least one real-time 3D position of the at least one surgical instrument may be obtained using a separate device including, but not limited to a separate instrument position sensor of a surgical instrument system. Non-limiting examples of suitable instrument position sensors include one or more electroanatomic mapping devices in addition to the electroanatomic mapping device 50 used to obtain the 3D endocardial surface mapping data, and other real-time position mapping systems that include position sensing devices that make use of ultrasound, magnetic fields, electrical fields, and/or any other existing suitable position sensing method.

In another aspect, additional data obtained by the electroanatomic mapping device 50 may include additional electrophysiological measurements obtained by one or more electrophysiology (EP) catheters. In one aspect, the data may include additional 3D real-time data defining one or more datasets of real-time electrophysiological measurements mapped to the coordinate system of the 3D model 65 of the heart 15. Non-limiting examples of real-time electrophysiological measurements include voltage maps, activation timing maps, and propagation maps. In this one aspect, the maps of additional electrophysiological measurements received by the computing device 30 may be overlaid on the 3D model 65 of the heart 15 within the holographic image. In an aspect, the maps of additional electrophysiological measurements may be selected for display, to be rendered transparent, or to be removed from the holographic image as defined by one or more cues produced by the operator. In another aspect, additional data obtained by the electroanatomic mapping device 50 may include additional electrophysiological measurements associated with ablation by an ablation catheter including, but not limited to, an amount of radiofrequency (RF) or cryoenergy applied at a particular position within the 3D model 65 of the heart 15. In this other aspect, the additional electrophysiological measurements may be incorporated into the holographic image in the form of a 3D visual element, such as a circle or other symbol positioned at the point of application of the ablation energy within the 3D model 65 and/or a color, size, numerical value or other visual element to indicate the amount and/or direction of the ablation energy or ablation force measured during ablation events enabled by the ablation catheter.

Figure 5A:
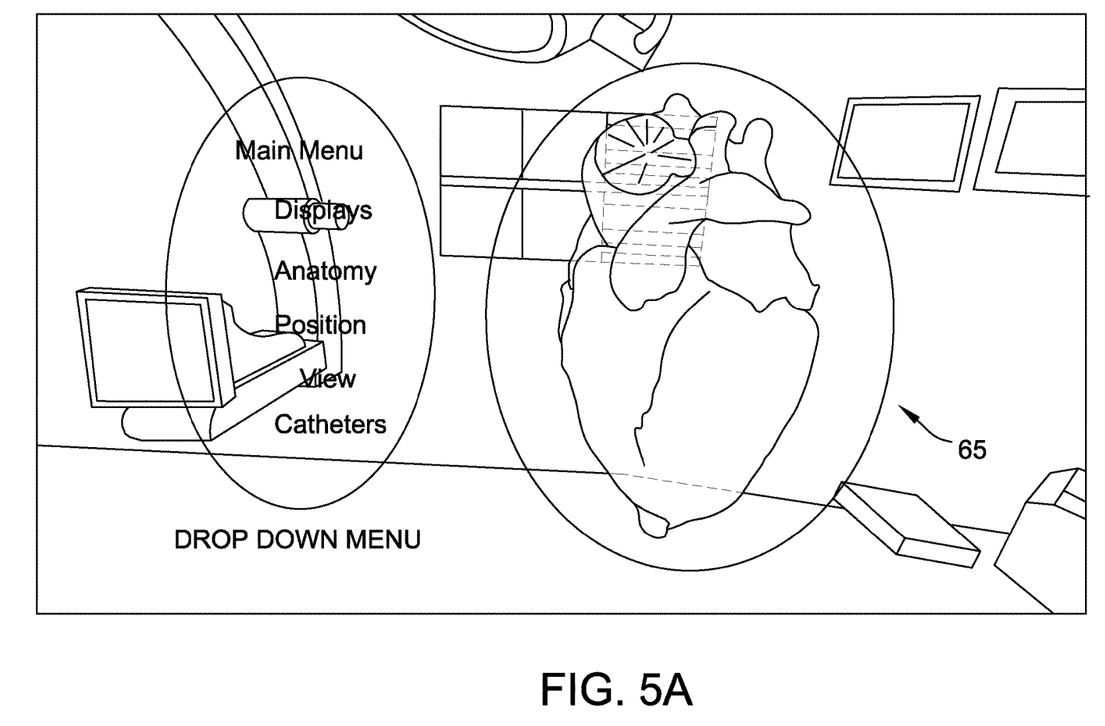
FIG. 5A is an image of a view provided to the operator of the VR/AR system that includes a drop-down menu according to one aspect.
Figure 5B:
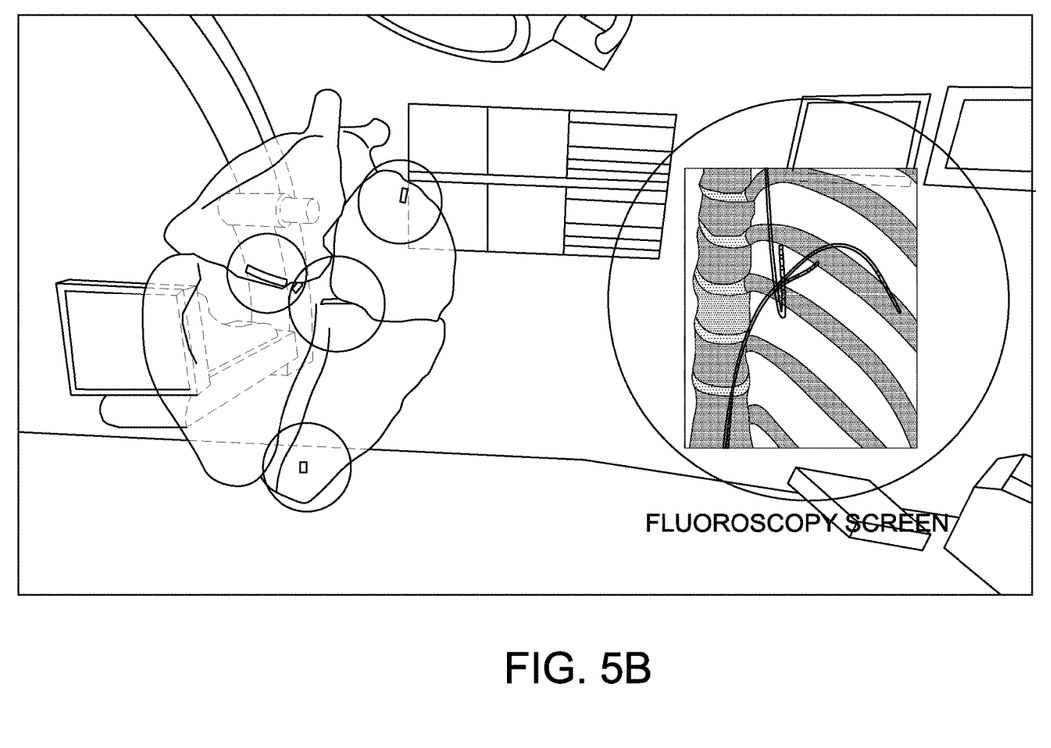
FIG. 5B is an image of a view provided to the operator of the VR/AR system that includes an inset image drop-down menu according to one aspect.

In an additional aspect, the computing device 30 may receive one or more additional datasets defining at least one additional 2D image obtained from at least one additional medical imaging device. In one aspect, the at least one additional 2D image may include a 2D representation of a 3D real-time image including, but not limited to, a real-time fluoroscope image. In this one aspect, the at least one additional 2D image may be incorporated into the holographic image in the form of a 2D visual element displayed separately from the 3D model 65. Non-limiting suitable 2D visual elements incorporated into the holographic image include a virtual 2D monitor, an inset image, and any other known representation of a 2D visual element in a 3D holographic image. By way of non-limiting example, an additional dataset defining a real-time fluoroscopic image may be incorporated into the holographic image in the form of an inset image, as illustrated in FIG. 5B.

In one aspect, the holographic image may be displayed on a holographic display of a VR/AR device 60 to an operator. In response to one or more cues from the operator, the computing device 30 may modify the holographic image as displayed on the holographic display according to the preferences of the operator. By way of non-limiting example, the operator may enlarge, reduce, rotate, or move the holographic image as displayed on the holographic display to facilitate the accomplishment of a diagnostic and/or surgical procedure. In various aspects, if the VR/AR system 10 includes multiple VR/AR devices 60, a first VR/AR device 60 worn by a first operator may be operatively coupled to the computing device 30 such that only the first operator may modify the holographic image as displayed on all holographic displays of all VR/AR devices 60 of the VR/AR system 10. In these various other aspects, the computing device 30 may receive the relative positions and orientations of each of the multiple VR/AR devices 60 and generate a holographic image for each VR/AR device 60 corresponding to each position and each orientation of each VR/AR device 60 relative to the first VR/AR device 60 worn by the first operator, who also controls modifications of the holographic image.

In one non-limiting example, the computing device 30 may generate an electrocardiogram of a patient's heart for display in an inset image of the holographic image. The computing device 30 may receive an indication of a user input (i.e. a cue) from the VR/AR device 60 or a separate input device (e.g., a camera or motion sensor) to position virtual markers on the electrocardiogram without breaking sterility. Based on the user input, the computing device 30 may determine a metric for display on the inset image along with the electrocardiogram. For instance, the virtual markers may be virtual calipers configured to measure a period or amplitude of the patient's heartbeat (e.g. a metric).

In another additional aspect, the computing device 30 may receive one or more additional alphanumeric datasets including, but not limited to, a patient demographic dataset and/or real-time measurements of vital signs of the subject obtained from existing vital sign measurement devices. In this other aspect, the one or more additional alphanumeric datasets may be incorporated into the holographic image in the form of a transparent alphanumeric element overlaid within the holographic image.

In additional aspects, the computing device 30 may generate a menu or other image element that includes user-selectable elements displayed in the form of a non-transparent or transparent row or column of alphanumeric strings, symbols, and/or icons. In these additional aspects, the user-selectable elements provide a means of selecting one or more instructions to be executed by one or more processors of the computing device 30 to enable the operation of the VR/AR system 10. By way of non-limiting example, the computing device 30 may generate a transparent menu within the holographic image as illustrated in FIG. 5A.

By selecting one or more of the interactive menu elements within the holographic image, the operator of the VR/AR device 60 can also view and interact with the 3D model 65 and additional information without having to break sterility or communicate with anyone present during a diagnostic or surgical procedure. As disclosed herein, the VR/AR device 60 can present and remove the information as needed in a true virtual reality environment or an augmented reality environment depending on the needs of the operator of the system 10. In one aspect, an arrangement of elements within the holographic image may be saved by the computing device 30 and retrieved by the VR/AR system 10 for subsequent use by the same operator as a preferred arrangement of elements.

In various aspects, the computing device 30 may update the holographic image over time to account for changes due to one or more time-varying factors including, but not limited to: section or deselection of a user-selectable menu element by the operator, receipt of updated real-time data such as updated vital signs data, an additional ablation event, a change in other datasets, such as the real-time dataset associated with the fluoroscope imaging. The computing device 30 may update the holographic image to include a representation of a portion of an instrument positioned relative to a patient's organ, e.g., a position of a catheter tip relative to the patient's heart. The computing device 30 may update the holographic image based on sensor data from the instrument indicative of detected motion of the instrument.

In an aspect, the computing device 30 of the VR/AR system 10 is configured to receive a reconstructed 3D model 65 of the patient's cardiac anatomy. Here, the 3D medical imaging device 40 is configured to acquire specific physical information related to the patient's heart 15. The information will encode the dimensions of the heart 15 and its components/cavities and pre-defined anatomical landmarks. These anatomically distinct landmarks are used to register the 3D model 65 to the electroanatomic map of the endocardial surface obtained by the electroanatomic mapping device 50. By registering the electroanatomic map to the coordinate system within which the 3D anatomical model, other measurements obtained by the electroanatomic mapping device 50 that are mapped to the electroanatomic map of the endocardial surface are also registered to the coordinate system defining the 3D model 65 of the heart 15, enabling these mapped electrophysiological measurements to be visualized with respect to the 3D model 65 within the holographic image displayed to the operator. In some aspects, the 3D model 65 and the electroanatomic map are generated in different physical units. Thus, to normalize to the same coordinate system, the computing device 30 registers (e.g., maps) a first set of points of the 3D model 65 to a second set of points of the electroanatomic map, e.g., based on the anatomical landmarks.

In various aspects, the registration of the electroanatomic map of the endocardial surface to the 3D anatomical model obtained using the at least one 3D medical imaging device is performed by the computing device 30 and/or the electroanatomic mapping device 50. The registration of the two maps may be performed using any suitable existing method without limitation. In one aspect, at least several pre-determined landmarks are identified in the 3D anatomical model and in the 3D endocardial surface map to provide defined points of intersection of the two maps. Non-limiting examples of suitable cardiac landmarks include the superior vena cava/right atrial junction, the inferior vena cava/right atrial junction, the coronary sinus, the right ventricular apex, and the right ventricular outflow tract. While landmarks associated with other known sections of the heart can be used for landmarks in other aspects of the disclosure, these landmarks are easy to access and identify, via MRI and fluoroscopic processes, and registered with the mesh, as discussed in more detail below. In other aspects, statistical or feature-based inference can be used to determine the location and number of points.

In an aspect, the 3D medical imaging device 40 can include any device that is capable of capturing 3D data related to the anatomy of the heart. For example, the 3D medical imaging device can include, but is not limited to, fluoroscopic devices, echocardiogram devices (e.g., transthoracic, transesophageal, intracardiac), X-ray devices, exploratory endoscopic systems, MRI and CT scanners, and the like. A 3D medical imaging device 40 may be selected depending on the type of diagnostic and/or surgical procedure to be performed in combination with the VR/AR visualization system 10. For example, an echocardiogram device 40 provides for a rapid acquisition of cardiac anatomy because it is non-invasive, can be done quickly, does not expose the patient to radiation, and is anesthesia-free. Further, there is not a prolonged requirement of immobility of the subject. In one aspect, data defining the reconstructed 3D anatomical model may be obtained and analyzed by the 3D medical imaging device 40 prior to a diagnostic or surgical procedure performed in combination with the use of the VR/AR visualization system 10.

The 3D medical imaging device 40 captures the spatial information used to reconstruct the 3D model 65 of the subject's heart 15. In one aspect, the 3D medical imaging device 40 reconstructs the spatial data and creates a 3D anatomical model of the subject's cardiac anatomy. Various techniques known in the art can be used to create the 3D anatomical model. By way of non-limiting example, multiple 2D views of the patient's heart can be collected and then re-assembled into a coarse 3D image of the patient's anatomy. Once the 3D image of the patient's anatomy is generated, the electroanatomic mapping device 50 provides, to the computing device 30, a generic high resolution heart mesh to be modified and/or transformed to match the overlap of the respective landmarks identified in the anatomical heart model and the electroanatomical endocardial surface model. The computing device 30 transforms the heart mesh using the data captured from the created 3D image of the patient's cardiac anatomy, including the spatial dimensions of the captured landmarks (discussed above). Once transformed, a full 3D model 65 of the cardiac structure of the patient is generated by the computing device 30 or the electroanatomic mapping device 50. By way of one non-limiting example, the 3D medical imaging device 40 may create a 3D anatomical model by generating a series of connected 2D polygons (e.g., a mesh) to represent 3D geometries of the corresponding anatomy. By way of another non-limiting example, the device 40 may create a 3D anatomical model using ray casting and/or tracing.

After the transformed full 3D model 65 of the patient's cardiac structure has been created at the electroanatomic mapping device 50, electroanatomic data, including electrophysiological data specific for the ablation needs are collected from the subject's and mapped to the transformed full 3D model 65. In an aspect, the electroanatomic data is collected from one or more electroanatomic mapping devices 50. In an aspect, the electroanatomic mapping devices 50 include electrophysiology (EP) catheters that are placed within the patient's heart 15. The measured electroanatomic data can include the electric activity (e.g., voltage data, activation timing, and propagation maps) that is occurring at a given location of the patient's heart 15, which can be used to determine where ablation needs to occur using existing diagnostic methods.

To perform an EP study, the VR/AR system 100 may use one or more electroanatomic mapping devices 50. In one aspect, diagnostic catheters 50 may be used initially, and an additional ablation catheter 50 may be used if ablation is indicated based on the diagnostic electrophysiological measurements. In addition, any energy applied by an ablation catheter 50 may be measured and recorded by the one or more electroanatomic mapping devices 50. By way of non-limiting example, ablation catheters may be configured to apply radiofrequency or cryoenergy at the catheter's tip. In another aspect, an ablation catheter may be configured to sense the level of force applied by the catheter (including directionality i.e. axial or lateral) at the tip of the catheter 50. Such information can be used to model the actual lesion creation in the virtual heart of the 3D model 65 as the lesion is being made in real-time by using measured force and impedance. In one aspect, the force data measured from the ablation catheter can then be used for auditory feedback to the operator with the VR/AR device 60. By way of non-limiting example, the VR/AR device 60 may provide auditory feedback including varying pitch and frequency of tones, indicative of the force level of the ablation catheter 50 pushing on the cardiac tissue.

The EP catheters 50 may be moved by the operator throughout the patient's heart 15 and collect diagnostic information. Both diagnostic and ablation catheters 50 are configured to obtain electroanatomic data throughout their use, including during ablation. In addition to collecting the electroanatomic data, the VR/AR system 100 may also capture the spatial related information, i.e., where the electroanatomic data is occurring within the patient's heart, so that the electroanatomic data can be mapped to the transformed full 3D model. In an aspect, the electroanatomic mapping device 50 captures the positioning of instruments inside a patient as well. For example, when EP catheters 50 are employed, the positioning of the electrodes and the distal part of the shaft of the catheter 50 are captured. In an aspect, the electroanatomic mapping device 50 utilizes an electroanatomic mapping system to find the coordinates of the electroanatomic data. The mapping system is able to identify the X, Y, and Z coordinates of the EP catheters 50 within the heart 15, and then can place the electroanatomic data to the coordinates. For example, an electroanatomic mapping system such as ENSITE™ NAVX™ Navigation and Visualization and CARTO™ (Biosense Webster Systems) can be used to collect these data. However, other systems capable of providing such information can be used.

Figure 3:
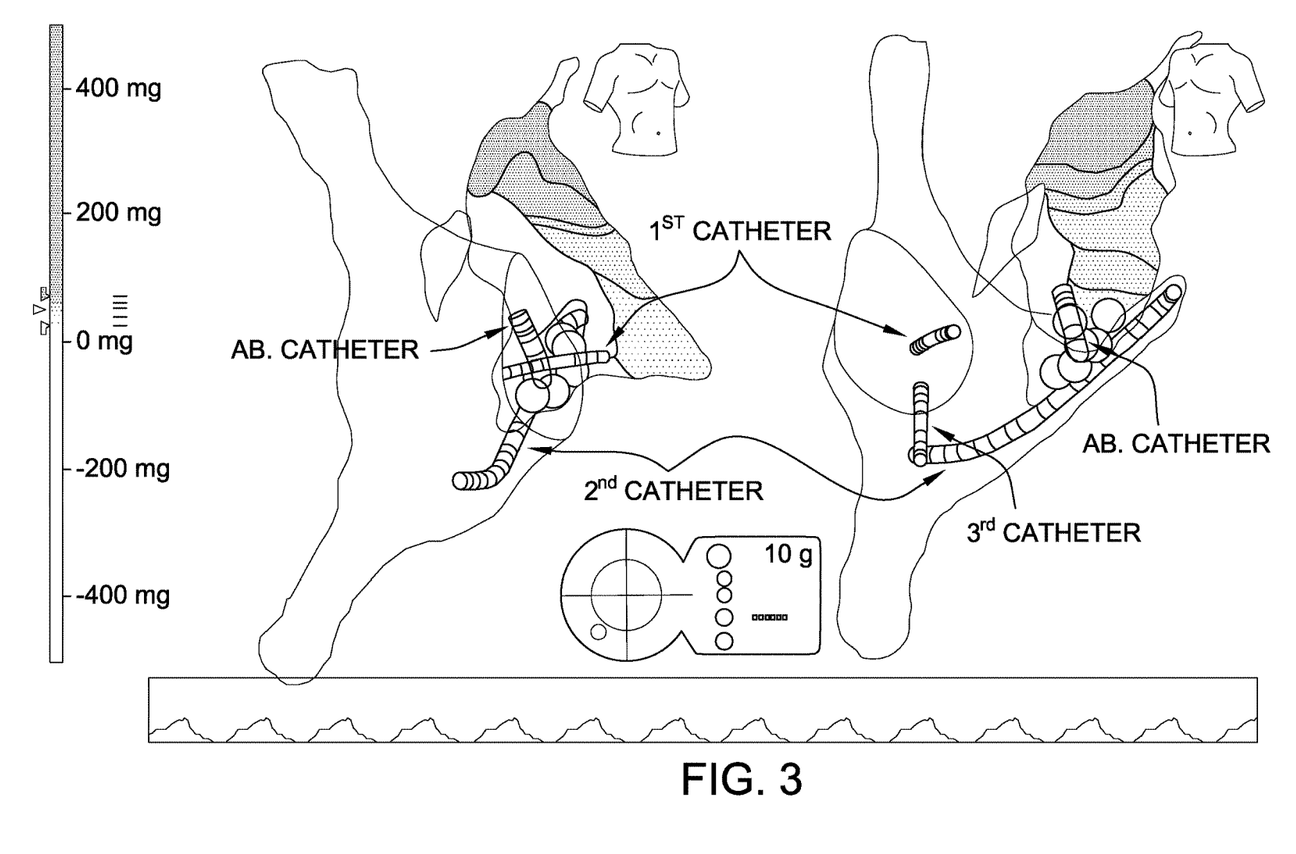
FIG. 3 is an image of an electroanatomic map according to an aspect of the present disclosure.

FIG. 3 illustrates an example of a current electroanatomic map for use in a cardiac model. This cardiac model is limited to the geometries of the right atrium (RA) and left atrium (LA). The image on the left is presented in orthogonal views, wherein a right anterior oblique (RAO) view is on the left and a long axial oblique (LAO) view is on the right. The distal ends of the electrophysiologic catheters are visualized inside this geometry. The first (1st) catheter, having four electrodes, is positioned at the site of normal conduction, at the His location. The 2nd catheter, having 10 electrodes, is positioned in the coronary sinus. The 3rd catheter, having 4 electrodes, is only visualized in the LAO projection as it is advanced through the tricuspid valve and into the right ventricle. Lastly, the radiofrequency (RF) ablation catheter, having 4 electrodes, is positioned at the site of abnormal electrical tissue. The spheres (shown in red) mark the sites where RF lesions were placed. The bullseye projection in the center bottom portion of FIG. 3 indicates the total force (TF) applied by the ablation catheter to cardiac tissue.

While the above describes electroanatomic mapping devices 50 and electroanatomic data associated with cardiac procedures, it is understood that the devices and data can be associated with other systems and organs found within the human body.

As the electroanatomic data is collected and mapped as described above, the VR/AR device 60 is provided with a 3D model 65 (see FIG. 4) of the patient's heart 15 by the computing device 30, including the placement of the EP catheters 50 (see FIG. 5B). In an aspect, the VR/AR device 60 can include a true virtual reality (VR) device (i.e., a device that fully immerses the operator in the created environment) or an augment reality (AR) device (i.e., operator can have images or models displayed virtually in the virtual space, but is still able to see and interact with the true environment). Along those lines, the VR/AR device 60 can be a wearable device, including, but not limited to, the Microsoft HOLOLENS™ (i.e. an AR device) and OCULUS RIFT™ (i.e. VR device). The VR/AR device 60 may include sensors such as motion sensors (e.g., accelerometers, gyroscopes, or inertial measurement units), audio sensors, eye and gaze tracking sensors, and/or an electronic display, among other components. In another aspect, the VR/AR device 60 can provide a projected holographic display that includes the 3D model 65. The VR/AR device 60 may be communicatively coupled to the HMD via a wireless exchange protocol, or via a wired connection. In at least some aspects, use of an AR device may be advantageous since it allows the operator to see the patient and interact with the patient in real time while simultaneously viewing and interacting with the 3D model 65 and deriving the benefits of it, making for a safer patient experience.

Figure 4:
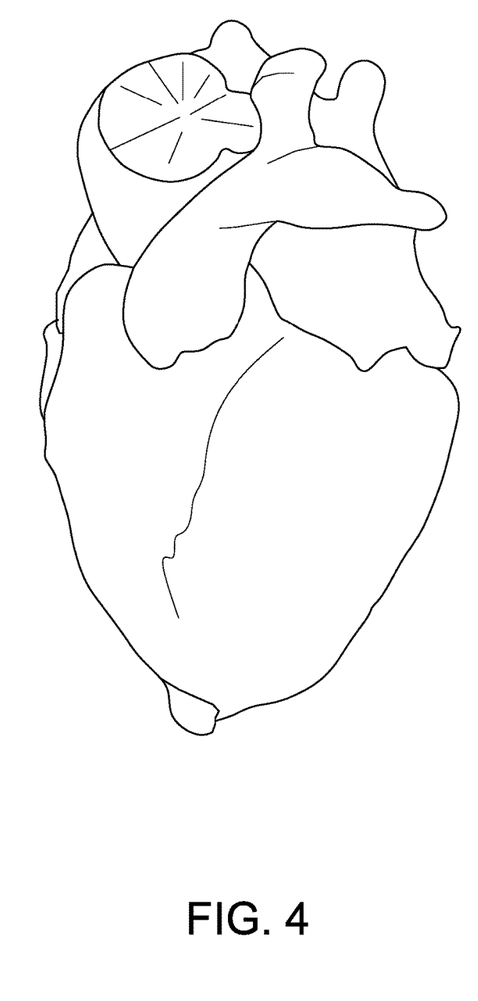
FIG. 4 illustrates a 3D model of a patient's heart according to an aspect of the present disclosure.

In such aspects, the 3D model 65 within the holographic image may be rendered as obtuse or semi-transparent depending on the location of the EP catheters, or fully transparent to enable an unimpeded view of the EP catheter positions. In a transparency view, the operator may change the transparency of the cardiac walls using operator-enabled cues received by at least one sensor of the VR/AR device, allowing for readily apparent visualization of the catheters in the heart during a diagnostic and/or surgical procedure. The portions of the catheter can also be represented throughout any view. In addition, the VR/AR device 60 can also allow the operator to manipulate the position, orientation, and size of the heart, as well as to create slices to view. Also, the operator can switch between views, as well as data display, without the use of hands so the operator can maintain sterility throughout the entirety of the procedure.

By way of non-limiting example, the VR/AR system 100 may use head and/or eye tracking technology to receive input commands (e.g., user input) from the operator without requiring the operator to physically touch an input device (e.g., VR/AR device 60) using the operator's hands. In some embodiments, the input device is physically connected to the VR/AR device 60. In other embodiments, the input device is separate from the VR/AR device 60 and communicatively coupled to the computing device 30. For example, the input device is a Microsoft KINECT™. The input device may include imaging sensors (e.g., cameras), illumination sources for the imaging sensors, motion sensors, depth sensors, among other components. Based on sensor data, the input device can capture hand gestures and perform posture detection of an operator. In one aspect, the operator-enabled inputs may be derived from modifications of existing operator-enabled inputs provided with the VR/AR device 60.

In addition, a planned mapping in preparation for an ablation procedure may be produced as well using the electroanatomic mapping devices 50 in combination with the VR/AR device 60, gathered from the collected electroanatomic data. In another aspect, virtual calipers (e.g., a ruler) can be displayed by the VR/AR device 60 to allow the operator, in the virtual environment, to make real time, accurate measurements. This feature allows the operator to make measurements in various places-for instance, when measuring electrograms, using milliseconds, and in the cardiac geometry, measuring in millimeters.

Other electroanatomic information can be displayed or communicated to the operator. For example, the electroanatomic information can be digitally represented on the 3D model 65 of the heart (e.g. color-coded areas on the heart to indicate electric activity and the force data of the EP catheter as it is applied), displayed visually to the operator (e.g., a table showing the relevant force data and electric activity), or in an auditory fashion. In an aspect, the auditory fashion can be used to inform the operator of the force that is being applied by the EP catheter as it is activated during the ablation procedure. In such instances, the auditory response can be proportional to the force as it is applied. The auditory signal relates to the force being applied by the ablation catheter. The stronger the force applied, the more frequent and high pitch the tone will sound for the operator. This auditory feature will only be present of force sensing catheters. An example of a force sensing catheter is the TACTICATH™ (St Jude Medical), which provides feedback to the operator indicating how much force the tip of the catheter is applying to tissue (e.g. measured in grams).

Figure 5C:
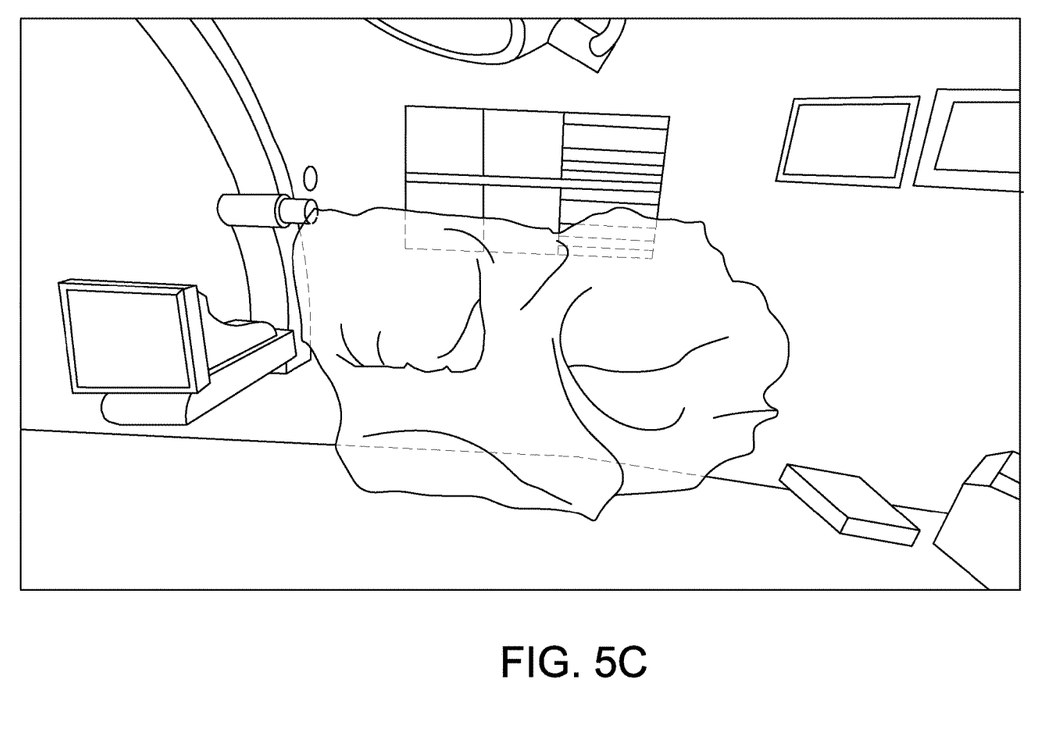
FIG. 5C is an image of a view provided to the operator of the VR/AR system that includes a cross-sectional view of a 3D heart model according to one aspect.

FIGS. 5A, 5B, and 5C illustrate exemplary views of the holographic images displayed by the VR/AR device 60 according to one aspect of the disclosure. FIG. 5A illustrates a main menu with a 3D model 65, a virtual cardiac model, turned on. The transparency of the 3D cardiac model 65 in this view is increased to allow the operator to quickly visualize precise catheter location in one or more planes without the need to change the model's orientation. In various aspects, the computing device 30 of the VR/AR system may segment the 3D model into subunits to facilitate selection of portions of the 3D model 65 for modifying the holographic display by rendering a portion of the 3D model 65 transparent and/or invisible. Non-limiting examples of subunits of the 3D model 65 that may be segmented by the computing device 30 include left and right atria, left and right ventricles, one or more valves, one of more arteries and veins associated with the heart, and any other relevant cardiac structure.

FIG. 5B illustrates a 3D model 65 displayed in a posterior projection with the catheter locations turned on, with part of the heart cut away using a cutting plane feature so that intracardiac catheter locations can be visualized. In this view, four catheters (circled) are seen positioned in the coronary sinus (in the atrioventricular groove separating the left atrium from left ventricle; towards the left side of the screen), the high right atrium (in the upper rightward chamber, near the right atrial/superior vena cava junction), in the right ventricular apex (in the lower rightward chamber, pointing towards the apex of the heart) and the normal His-conduction system (towards the center, or crux, of the heart). In some aspects, the computing device 30 includes additional components in the displayed 3D model 65 based on an operator-controlled level of zoom (e.g., magnification/reduction) of the holographic display. For example, at a greater level of zoom (i.e., magnified image), the computing device 30 includes one or more of the four catheters shown in FIG. 5B. On the other hand, at a lower level of zoom (i.e., reduced image), the computing device 30 does not include the four catheters, e.g., due to a resulting limited level of resolution of the displayed 3D model 65. To the right in FIG. 5B, the fluoroscopy screen has been turned on in the virtual environment.

FIG. 5C shows the 3D model 65 displayed as oriented in a down-the-barrel view (i.e., a surgeon's view) of the ventricles, with the atria and great arteries virtually removed, e.g., a cross-sectional view. These images provide non-limiting examples of potential views that an operator may see using the VR/AR system 10, and should not be construed as the only views provided by the system 10 of the disclosure.

Figure 6:
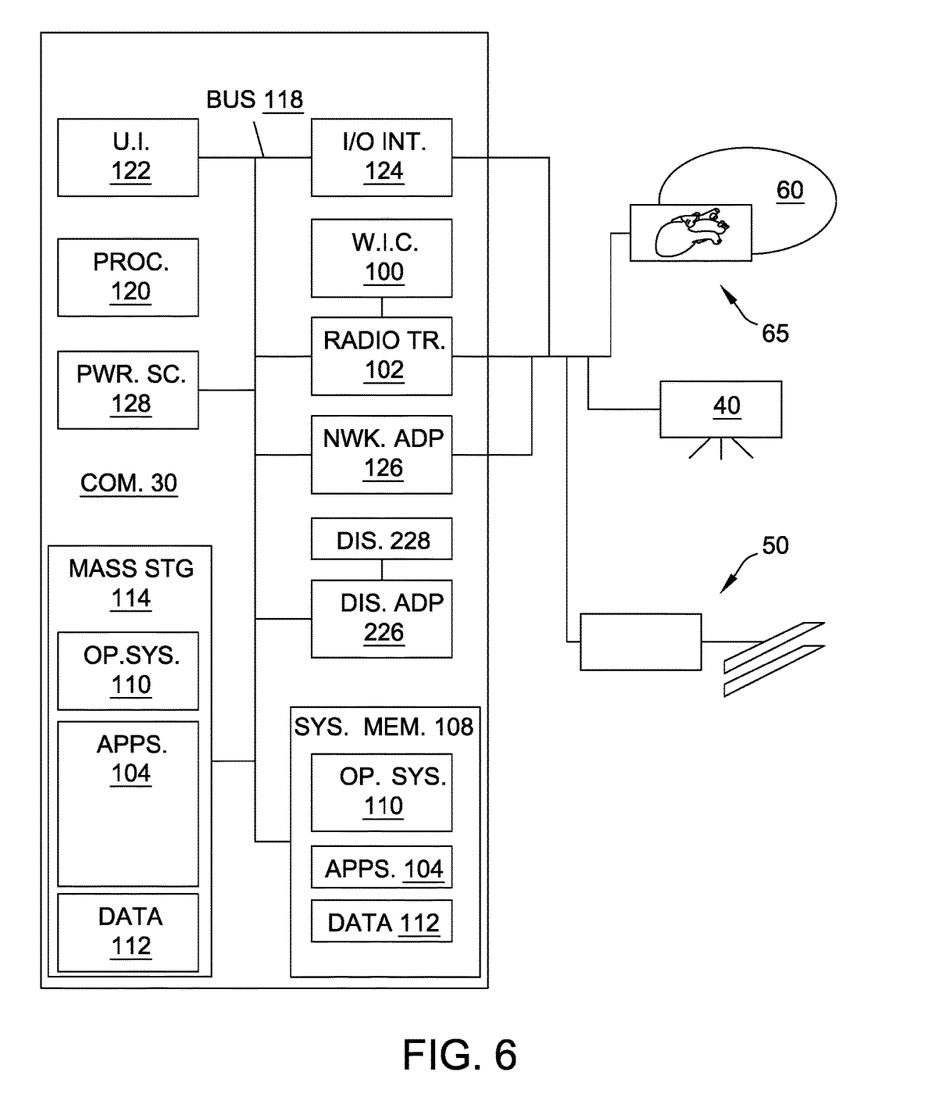
FIG. 6 is a block diagram showing a schematic representation of components of the VR/AR system of FIG. 2.

In various aspects, the computing device 30 can include, but is not limited to, laptop computers, desk top computers, tablets, servers with a connected display and the like. According to an aspect, as shown in FIG. 6, the computing device 30 can communicate with the 3D medical imaging device 40, the electroanatomic mapping device 50, and the VR/AR device 60 through various known means, including wired and wireless connections known in the art. In an aspect, the computing device 30 can include a wireless interface controller ("W.I.") 100 configured to control the operation of the radio transceiver 102, as well as the receiving and sending of information from the other devices. The radio transceiver 102 may communicate on a wide range of public frequencies, including, but not limited to, frequency bands 2.40 Hz and/or 5 GHz-5.8 GHz. In addition, the radio transceiver 102, with the assistance of the wireless interface controller 100, may also utilize a variety of public protocols. For example, in some embodiments of the disclosure, the combination wireless interface controller 100 and radio transceiver 102 may operate on various existing and proposed IEEE wireless protocols, including, but not limited to, IEEE 802.11 b/g/n/a/ac, with maximum theoretical data transfer rates/throughput of 11 Mbps/54 Mbps/600 Mbps/54 Mbps/1 Gbps respectively. In an aspect, the computing device 30 may include a network adapter 126 configured to communicate with other devices over various networks and connections.

The computing device 30 may have one or more software applications 104 to perform the methods discussed above. The computing device 30 includes system memory 108, which can store the various applications 104, including applications to carry out functions discussed above, as well as the operating system 110. The system memory 108 may also include data 112 accessible by the various software applications 104. The system memory 108 can include random access memory (RAM) or read only memory (ROM). Data 112 stored on the computing device 30 may be any type of retrievable data. The data may be stored in a wide variety of databases, including relational databases, including, but not limited to, Microsoft Access and SQL Server, MySQL, INGRES, DB2, INFORMIX, Oracle, PostgreSQL, Sybase 11, Linux data storage means, and the like.

The computing device 30 can include a variety of other computer readable media, including a storage device 114. The storage device 114 can be used for storing computer code, computer readable instructions, program modules, and other data 112 for the computing device 30, and the storage device 114 can be used to back up or alternatively to run the operating system 110 and/or other applications 104. The storage device 114 may include a hard disk, various magnetic storage devices such as magnetic cassettes or disks, solid-state flash drives, or other optical storage, random access memories, and the like.

The computing device 30 may include a system bus 118 that connects various components of computing device 30 to the system memory 108 and to the storage device 114, as well as to each other. Other components of the computing device 30 may include one or more processors or processing units 120, a user interface (U.I.) 122, and one or more input/output interfaces 124. In addition, the computing device 30 includes a network adapter 126. In addition, the computing device 30 can included a power source 128, including, but not limited to, a battery or an external power source. In addition, the computing device 30 can include a display adapter 226 and a display 228 (e.g., a monitor or screen). In addition, input devices (e.g., key board, mouse, joy stick, etc.) can be used via the input output interfaces 124. Further, the other 3D medical imaging device 40, electroanatomic mapping device 50, and VR/AR device 60 can communicate with the computing device 30 via the input/output interfaces 124 as well.

The VR/AR system 10 is configured to display virtual, patient-specific 3D models 65 in front of interventional physicians (e.g., operators) during diagnostic and/or surgical procedures. By using 3D models 65 to reveal real-time electrophysiology, improvements in physician training, patient outcomes, and clinician collaboration will occur, as well as decrease radiation exposure rates to both the patient and physician. Further, the system 10 will also reduce the medical and economic burden for a patient who would otherwise undergo multiple procedures that result from poor visualization of their anatomy.

While the foregoing written description of the disclosure enables one of ordinary skill to make and use what is considered presently to be the best mode thereof those of ordinary skill will understand and appreciate the existence of variations, combinations, and equivalents of the specific embodiment, method, and examples herein. The disclosure should therefore not be limited by the above described embodiments, methods, and examples, but by all embodiments and methods within the scope and spirit of the disclosure. To the extent necessary to understand or complete the disclosure, all publications, patents, and patent applications mentioned herein are expressly incorporated by reference therein to the same extent as though each were individually so incorporated.

Having thus described exemplary embodiments of the disclosure, those skilled in the art will appreciate that the within disclosures are exemplary only and that various other alternatives, adaptations, and modifications may be made within the scope of the disclosure. Accordingly, the disclosure is not limited to the specific embodiments as illustrated herein.

What is claimed is:

1. A system comprising:
    a catheter configured to be inserted inside a cardiovascular organ of a subject, the catheter comprising one or more sensors generating a first set of sensor data;
    a head-mounted display (HMD) configured to be worn by an operator and to display an electroanatomic visualization representing the cardiovascular organ in 3D in a field of view of the operator in response to receiving 3D images, wherein the 3D images include at least a first 3D image and a second 3D image;
    an input device configured to generate a second set of sensor data responsive to a motion of the operator; and
    one or more computers communicatively coupled to the catheter to receive the first set of sensor data, communicatively coupled to the input device to receive the second set of sensor data, and communicatively coupled to the HMD via a wireless data exchange protocol, wherein the one or more computers comprises one or more processors and computer program instructions that when executed cause the one or more processors to:
  generate the first 3D image by processing the first set of sensor data;
  provide the first 3D image to the HMD;
  receive the second set of sensor data responsive to the motion of the operator to interact with the electroanatomic visualization;
  determine a path of the motion of the operator by processing the second set of sensor data;
  determine an angle of rotation for the electroanatomic visualization based on the path of the motion; and
  provide the second 3D image to the HMD to update the display of the electroanatomic visualization by rotating the cardiovascular organ by the angle of rotation in the field of view of the operator.

2. The system of claim 1, wherein the operator performs at least one of the motions using a hand of the operator, and wherein the hand does not physically contact the input device while the operator performs the at least one of the motions.

3. The system of claim 1, wherein the one or more sensors include at least one of an impedance sensor, a magnetic sensor, and an ultrasound sensor.

4. The system of claim 1, wherein the one or more computers include further computer program instructions that when executed cause the one or more processors to:
  provide a third 3D image to the HMD to display an electrocardiogram of the cardiovascular organ in the field of view of the operator;
  receive from the input device, a third set of sensor data indicative of subsequent motion of the body part of the operator to position one or more virtual markers on the electrocardiogram;
  determine a metric based on positions of the one or more virtual markers by processing the third set of sensor data; and
  provide the metric to the HMD to update the display of the electrocardiogram in the field of view of the operator.

5. The system of claim 4, wherein generating the first 3D image of the electroanatomic visualization comprises:
  mapping a first plurality of points of the first set of sensor data to a second plurality of points of the third set of sensor data in 3D, wherein the first set of sensor data and the third set of sensor data are generated in different physical units.

6. The system of claim 1, wherein generating the first 3D image of the electroanatomic visualization comprises:
  generating a series of connected 2D polygons to represent 3D geometries of the cardiovascular organ.

7. The system of claim 1, wherein the one or more computers include further computer program instructions that when executed cause the one or more processors to:
  provide, simultaneously with providing the second 3D image to the HMD, a third 3D image to another HMD worn by another operator to display the electroanatomic visualization rotated by the angle of rotation in another field of view of the another operator, wherein the another field of view is positioned at an offset angle from the field of view.

8. A method comprising:
  generating a first 3D image of an electroanatomic visualization representing a cardiovascular organ of a subject in 3D by processing a first set of sensor data generated by a catheter inserted inside the cardiovascular organ;
  providing the first 3D image to a head-mounted display (HMD) worn by an operator to display the electroanatomic visualization in a field of view of the operator;
  receiving from an input device, a second set of sensor data indicative of motion of a body part of the operator to interact with the electroanatomic visualization;
  determining a path of the motion of the body part by processing the second set of sensor data;
  determining an angle of rotation for the electroanatomic visualization based on the path of motion; and
  providing a second 3D image to the HMD to update the display of the electroanatomic visualization by rotating the cardiovascular organ by the angle of rotation in the field of view of the operator.

9. The method of claim 8, further comprising:
  receiving a third set of sensor data indicative of another motion of the operator to select a command of a plurality of commands; and
  determining that the selected command corresponds to a rotation command by processing the third set of sensor data.

10. The method of claim 9, wherein the third set of sensor data is received from the HMD, and wherein the another motion is motion of a head of the operator.

11. The method of claim 8, wherein the input device is physically connected to the HMD.

12. The method of claim 8, further comprising:
  providing a third 3D image to the HMD to display an electrocardiogram of the cardiovascular organ in the field of view of the operator;
  receiving from the input device, a third set of sensor data indicative of subsequent motion of the body part of the operator to position one or more virtual markers on the electrocardiogram;
  determining a metric based on positions of the one or more virtual markers by processing the third set of sensor data; and
  providing the metric to the HMD to update the display of the electrocardiogram in the field of view of the operator.

13. The method of claim 8, further comprising:
  receiving from the input device, a third set of sensor data indicative of subsequent motion of the body part of the operator;
  determining an increase in a level of zoom of the electroanatomic visualization responsive to the subsequent motion; and
  providing a third 3D image to the HMD to display the electroanatomic visualization including one or more additional components in the field of view of the operator.

14. The method of claim 8, wherein the electroanatomic visualization further includes a representation of a portion of the catheter positioned relative to the cardiovascular organ in 3D.

15. The method of claim 14, further comprising:
  receiving a third set of sensor data from the catheter indicative of detected motion of the catheter; and
  providing a third 3D image to the HMD to update the display of the electroanatomic visualization by moving the portion of the catheter based on the detected motion in the field of view of the operator.

16. The method of claim 8, wherein the first 3D image is generated further by aggregating the first set of sensor data with a third set of sensor data generated by at least one of an impedance sensor, a magnetic sensor, and an ultrasound sensor.

17. The method of claim 16, wherein generating the first 3D image of the electroanatomic visualization comprises:
mapping a first plurality of points of the first set of sensor data to a second plurality of points of the third set of sensor data in 3D, wherein the first set of sensor data and the third set of sensor data are generated in different physical units.

18. The method of claim 8, wherein generating the first 3D image of the electroanatomic visualization comprises:
generating a series of connected 2D polygons to represent 3D geometries of the cardiovascular organ.

19. The method of claim 8, further comprising:
providing, simultaneously with providing the second 3D image to the HMD, a third 3D image to another HMD worn by another operator to display the electroanatomic visualization rotated by the angle of rotation in another field of view of the another operator, wherein the another field of view is positioned at an offset angle from the field of view.

20. A non-transitory computer readable storage medium having instructions encoded thereon that, when executed by a processor, cause the processor to perform steps including:
generating a first 3D image of an electroanatomic visualization representing a cardiovascular organ of a subject in 3D by processing a first set of sensor data generated by a catheter inserted inside the cardiovascular organ;
providing the first 3D image to a head-mounted display (HMD) worn by an operator to display the electroanatomic visualization in a field of view of the operator;
receiving from an input device, a second set of sensor data indicative of motion of a body part of the operator to interact with the electroanatomic visualization;
determining a path of the motion of the body part by processing the second set of sensor data;
determining an angle of rotation for the electroanatomic visualization based on the path of motion; and
providing a second 3D image to the HMD to update the display of the electroanatomic visualization by rotating the cardiovascular organ by the angle of rotation in the field of view of the operator.

21. The computer readable storage medium of claim 20, further comprising instructions that, when executed by the processor, cause the processor to perform steps including:
receiving a third set of sensor data indicative of another motion of the operator to select a command of a plurality of commands; and
determining that the selected command corresponds to a rotation command by processing the third set of sensor data.

22. The computer readable storage medium of claim 21, wherein the third set of sensor data is received from the HMD, and wherein the another motion is motion of a head of the operator.

23. The computer readable storage medium of claim 20, wherein the input device is physically connected to the HMD.

24. The computer readable storage medium of claim 20, further comprising instructions that, when executed by the processor, cause the processor to perform steps including:
providing a third 3D image to the HMD to display an electrocardiogram of the cardiovascular organ in the field of view of the operator;
receiving from the input device, a third set of sensor data indicative of subsequent motion of the body part of the operator to position one or more virtual markers on the electrocardiogram;
determining a metric based on positions of the one or more virtual markers by processing the third set of sensor data; and
providing the metric to the HMD to update the display of the electrocardiogram in the field of view of the operator.

25. The computer readable storage medium of claim 20, further comprising instructions that, when executed by the processor, cause the processor to perform steps including:
receiving from the input device, a third set of sensor data indicative of subsequent motion of the body part of the operator;
determining an increase in a level of zoom of the electroanatomic visualization responsive to the subsequent motion; and
providing a third 3D image to the HMD to display the electroanatomic visualization including one or more additional components in the field of view of the operator.

26. The computer readable storage medium of claim 20, wherein the electroanatomic visualization further includes a representation of a portion of the catheter positioned relative to the cardiovascular organ in 3D.

27. The computer readable storage medium of claim 26, further comprising instructions that, when executed by the processor, cause the processor to perform steps including:
receiving a third set of sensor data from the catheter indicative of detected motion of the catheter; and
providing a third 3D image to the HMD to update the display of the electroanatomic visualization by moving the portion of the catheter based on the detected motion in the field of view of the operator.

28. The computer readable storage medium of claim 20, wherein generating the first 3D image comprises:
aggregating the first set of sensor data with a third set of sensor data generated by at least one of an impedance sensor, a magnetic sensor, and an ultrasound sensor; and
mapping a first plurality of points of the first set of sensor data to a second plurality of points of the third set of sensor data in 3D, wherein the first set of sensor data and the third set of sensor data are generated in different physical units.

29. The computer readable storage medium of claim 20, wherein generating the first 3D image of the electroanatomic visualization comprises:
generating a series of connected 2D polygons to represent 3D geometries of the cardiovascular organ.

30. The computer readable storage medium of claim 20, further comprising instructions that, when executed by the processor, cause the processor to perform steps including:
providing, simultaneously with providing the second 3D image to the HMD, a third 3D image to another HMD worn by another operator to display the electroanatomic visualization rotated by the angle of rotation in another field of view of the another operator, wherein the another field of view is positioned at an offset angle from the field of view.

* * * * *